United States Patent
Grözinger et al.

(10) Patent No.: US 7,834,334 B2
(45) Date of Patent: Nov. 16, 2010

(54) PARTICLE THERAPY SYSTEM

(75) Inventors: Sven Oliver Grözinger, Herzogenaurach (DE); Klaus Herrmann, Nürnberg (DE); Eike Rietzel, Darmstadt (DE); Andres Sommer, Langensendelbach (DE); Torsten Zeuner, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 385 days.

(21) Appl. No.: 12/092,692

(22) PCT Filed: Nov. 8, 2006

(86) PCT No.: PCT/EP2006/068228

§ 371 (c)(1),
(2), (4) Date: May 15, 2008

(87) PCT Pub. No.: WO2007/054511

PCT Pub. Date: May 18, 2007

(65) Prior Publication Data

US 2008/0237495 A1    Oct. 2, 2008

(30) Foreign Application Priority Data

Nov. 10, 2005    (DE) .................. 10 2005 053 719

(51) Int. Cl.
*G01G 5/00*    (2006.01)

(52) U.S. Cl. .................. 250/492.3; 250/492.1; 600/1; 600/2

(58) Field of Classification Search .............. 250/492.1, 250/492.3; 600/1, 2
See application file for complete search history.

(56) References Cited

U.S. PATENT DOCUMENTS

| 5,117,829 | A | 6/1992 | Miller et al. |
| 6,094,760 | A | 8/2000 | Nonaka et al. |
| 6,683,318 | B1 | 1/2004 | Haberer et al. |
| 2005/0161618 | A1 | 7/2005 | Pedroni |

(Continued)

FOREIGN PATENT DOCUMENTS

EP    0 986 070 A1    3/2000

(Continued)

OTHER PUBLICATIONS

Written Opinion dated Feb. 2006.

(Continued)

*Primary Examiner*—Jack I Berman
*Assistant Examiner*—Hanway Chang
(74) *Attorney, Agent, or Firm*—Brinks, Hofer, Gilson & Lione

(57) ABSTRACT

A particle therapy system for irradiating a volume of a patient to be irradiated with high-energy particles is provided. The system includes a radiation outlet of a radiation delivery and acceleration system from which a particle beam exits in order to interact with the patient positioned in an irradiation position; an imaging device for verifying the position of the volume to be irradiated in relation to the particle beam; and a patient-positioning device with which the patient can be brought into the irradiation position for irradiation. The imaging device checks the position of the volume to be irradiated in an imaging position of the patient that is spatially remote from the irradiation position, and the patient-positioning device automatically changes position between imaging position and irradiation position.

18 Claims, 2 Drawing Sheets

U.S. PATENT DOCUMENTS

2008/0023644 A1    1/2008    Pedroni

FOREIGN PATENT DOCUMENTS

| EP | 1 584 353 A1 | 10/2005 |
| JP | 11 009708 | 1/1999 |
| WO | WO 90/11721 | 10/1990 |
| WO | WO 01/78514 A2 | 10/2001 |
| WO | WO 03/020196 A3 | 3/2003 |

OTHER PUBLICATIONS

International Search Report dated Feb. 26, 2007.
H. Blattmann in "Beam delivery systems for charged particles," Radiat. Environ. Biophys. (1992) 31:219-231 discloses various irradiation systems and techniques.

PARTICLE THERAPY SYSTEM

The present patent document is a §371 continuation of PCT Application Serial Number PCT/EP2006/068228, filed Aug. 11, 2006, designating the United States, which is hereby incorporated by reference. This patent document also claims the benefit of DE 10 2005 053719.7, filed Oct. 11, 2005.

BACKGROUND

The present embodiments relate to a particle therapy system.

A particle therapy system (installation) may be used to irradiate a patient with a particle beam. H. Blattmann in "Beam delivery systems for charged particles," Radiat. Environ. Biophys. (1992) 31:219-231 discloses various irradiation systems and techniques. EP 0 986 070 discloses a particle therapy system.

Japanese Patent Disclosure JP 11009708 A discloses an irradiation therapy system, in which a patient positioning device is located between a magnetic resonance scanner and the gantry of a treatment system.

A particle therapy system includes an accelerator unit and a high-energy beam guiding system. A synchrotron or a cyclotron is used to accelerate the particles, such as protons, pions, or helium, carbon or oxygen ions.

The high-energy beam guiding (transport) system carries the particles from the accelerator unit to one or more treatment chambers. In a "fixed beam" treatment chamber, the particles reach the treatment site from a fixed direction. In a gantry-based treatment chambers, the particle beam may be aimed at the patient from various directions.

The particle therapy system includes a monitoring and safety system that assures that a particle beam, which is characterized by the required parameters, is carried into the appropriate treatment chamber. The parameters are defined in a treatment or therapy plan. The plan indicates how many particles, from what direction, and how much energy, should strike the patient.

The therapy plan is created using an image data set. For instance, a three-dimensional (3D) data set is created with a computed tomography scanner. The tumor is located within the image data set, and the required radiation doses and directions of incidence are decided based on the image data set.

During the radiation treatment (irradiation), the patient assumes an irradiation position on which the treatment planning was based. For a fixation mask is used. Before the irradiation, the position of the patient is checked with an imaging device. The current irradiation position may be calibrated with the image data set on which the treatment planning was based.

Before the radiation treatment (irradiation), images from various directions are calibrated, for example, with projections from a CT planning data set. Scans may be made in the beam direction and orthogonally to the beam direction. The scans are made in the irradiation position near the beam exit. There may be only a limited amount of space for the imaging.

A 3D image data set may be obtained based on performing scans from various directions. From the image data, a 3D image data set may be obtained, similarly to a CT scan. For scanning a patient from various directions, an imaging robot arm may be aimed freely around a patient. Another option is obtaining a 3D image data set using a C-arm X-ray machine, for example.

The imaging units for obtaining 3D image data sets from various directions require enough space to enable scanning the patient from different directions. Elements of the imaging unit are capable of being moved around the patient at a sufficient distance for imaging.

In particle therapy, patient is positioned close to the beam exit, to keep the flaring of the stream from scattering. For example, a typical spacing between the isocenter of an irradiation site and the beam exit is approximately 60 cm.

The spacing between the isocenter of an irradiation site and the beam exit restricts the imaging for position verification to imaging devices that occupy correspondingly little space.

SUMMARY AND DESCRIPTION

The present embodiments may obviate one or more of the limitations or drawbacks inherent in the related art. For example, in one embodiment, a particle therapy system is used to plan and perform an irradiation of a patient using a 3D imaging technique.

In one embodiment, a particle therapy system for irradiating a volume to be irradiated of a patient with high-energy particles is provided. The system includes a beam exit, an imaging device, and a patient positioning device. The beam exit includes an aperture that allows a particle beam to exit a radiation delivery and acceleration system. The beam exit directs the particle beam exits into the patient, who is positioned in an irradiation position. The irradiation position is specified in a therapy plan relative to an irradiation isocenter. The imaging device verifies the location of the volume to be irradiated with respect to the particle beam. The patient positioning device is operable to position the patient for the irradiation in the irradiation position. The imaging device is used to verify the location of the volume to be irradiated in an imaging position of the patient that is spatially distant from the irradiation position. The patient positioning device is operable to automatically change positions between the imaging position and the irradiation position.

In one embodiment, the imaging device is used to verify that the location of the volume to be irradiated in an imaging position of the patient. The imaging position is spatially distant from the irradiation position. The imaging position has at least the minimum spacing necessary for 3D imaging between the imaging device and the beam exit.

The imaging position is located between the patient positioning device and the irradiation position. The travel distance from the imaging position to the irradiation position and back is short. The patient positioning device is controlled, for example, by a monitoring system, which implements a suitable therapy plan and which may bring about the change of position between the imaging position and the irradiation position.

In one embodiment, an optimal spacing from the beam exit may be set, without having to dispense with 3D imaging because of an imaging device that takes up a corresponding amount of space. Accordingly, a particle beam may be used for precise irradiation. The beam exit may be disposed close to the isocenter. Accordingly, the particle beam diverges less and has a narrow beam diameter. The position verification may be done with 3D or at least 3D-like data sets.

In one embodiment, an imaging center is located with the irradiation isocenter on a center axis of the beam. The imaging center may be assigned to the imaging position. The term "center axis of the beam" is the beam course defined by the neutral position of a raster scanner.

In one embodiment, the distance between the irradiation isocenter and the imaging center may be equal to or less than 2 m, preferably less than 1 m and if possible less than 0.5 m. During an irradiation, the position verification may be done multiple times. For example, without major loss of time from long travel distances. The imaging center, for example, may be at or nearly at the minimum spacing from the irradiation isocenter. The displacement of the patient may be as little as possible.

In one embodiment, the patient positioning device includes a robotically (automatically) triggered treatment table. The patient positioning device is triggered by a therapy monitoring unit of the particle therapy installation. The parameters that are used to perform (cause) a change of position, for example, may be stored in memory in the therapy plan, which may be the basis for the therapy monitoring unit for controlling the irradiation.

A therapy plan is a data set, made (generated), for example, by a computer unit, in which patient-specific data, among other data, are stored in memory. The data may, for example, include a medical copy of the tumor to be treated, and/or selected regions to be irradiated in the body of a patient, and/or organs at risk, whose radiation exposure should be minimal. The data may include, for example, parameters that characterize the particle beam and that indicate how many particles, from what direction, with how much energy, are to strike the patient, or certain regions to be irradiated. The energy of the particles determines the penetration depths of the particles into the patient, or the location of the voxel where the maximum interaction with the tissue in the particle therapy takes place, or the location where the maximum dose is deposited. From the therapy plan, the therapy monitoring unit may ascertain the control instructions required for controlling the irradiation.

In one embodiment, a therapy plan may include a reference point for positioning the patient in an imaging position or irradiation position, and information about the relative position of the imaging position and irradiation position, with respect to each other. The therapy plan may include a displacement vector, which defines a displacement motion of a patient supporting device of the therapy installation, with which device the patient may be displaced from the imaging position into the irradiation position. The displacement vector may be parallel to a beam axis of the particle beam.

The irradiation isocenter or its spacing from the beam exit may be defined in the therapy plan, for example, during the treatment planning. The position verification may be done independently of the irradiation position.

DETAILED DESCRIPTION

Figure 1:
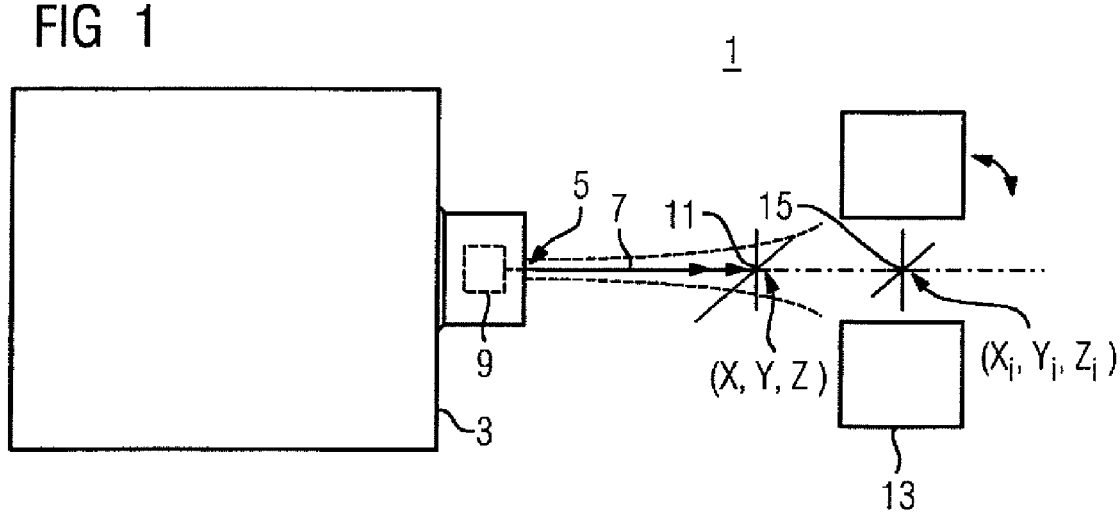
FIG. 1 illustrates one embodiment of a particle therapy system.

FIG. 1 shows a particle therapy system (installation) 1 for irradiating a volume of a patient with high-energy particles. The system 1 includes a particle accelerator system 3 that emits a particle beam 7 from a beam exit 5. The particle therapy system 1 may include a raster scanner 9 that may scans a region, for example, of 40 cm×40 cm. An isocenter 11 may be located centrally in the scanning region. The particle beam 7 diverges because of scattering processes in the beam or with the material being scanned. The isocenter is located as close as possible to the beam exit 5, so that irradiation may be done with the smallest possible beam diameter. During irradiation with protons, a spacing of 60 cm may be selected. At 60 cm, the beam diverges to the desired beam size assumed in the therapy plan. For example, the irradiation is done with a raster scanning method and a beam diameter of approximately 3 to 5 mm.

The particle therapy system 1 may include an imaging device 13. The imaging device 13 may be used to generate a 3D data set of the region of the volume to be irradiated. The imaging device 13 may be used to verify the position of the volume to be irradiated with respect to the particle beam 7. The imaging device 13 has an imaging center 15. The spacing of the imaging center 15 from the beam exit 5 may be greater than the spacing of the irradiation isocenter 11 from the beam exit 5 depending on the dimensions and structure of the imaging device 13. The imaging center 15 is located on the center axis of the beam. The spacing between the irradiation isocenter 11 and the imaging center 15 is as small as possible, for example, the spacing of the irradiation center 15 from the beam exit 5 is 100 cm. A displacement in or counter to the beam direction of 40 cm is quick and performed without burdening the patient, even during an irradiation session.

Figure 2:
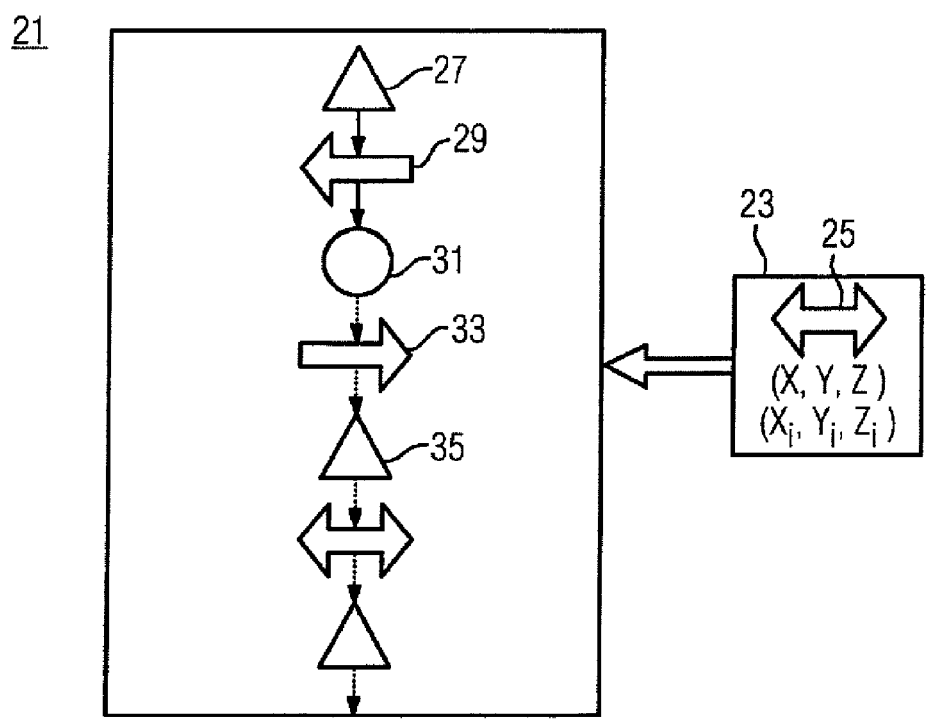
FIG. 2 illustrates a flow chart of one embodiment of a therapy plan.

FIG. 2 shows an irradiation session 21 that is being performed in accordance with a therapy plan 23. The therapy plan 23 includes required beam parameters, the particle energy, and particle intensity, for example, for various voxels of the volume to be irradiated. The therapy plan may include information about the location (X, Y, Z) of the irradiation isocenter and/or the location $(X_i, Y_i, Z_i)$ of the imaging center and/or a displacement vector 25.

The irradiation session 21 includes a position verification 27, which positions the patient, in accordance with the therapy plan 23, in the irradiation center (X, Y, Z) in the irradiation position. A displacement 29 is performed in accordance with the displacement vector 25. The patient is in the irradiation position. In the irradiation position, a first irradiation procedure 31 is performed.

A second displacement 33 may be performed during the irradiation, back to the irradiation position, for example, when the position of the patient has changed. A further position verification 35 may be performed.

Position verifications 27, 35 may occur repeatedly, either because of suspected changes of position, for safety reasons, or to perform a further irradiation, for example, from a different direction of incidence.

A therapy plan 23, on which the irradiation session 21 is based, may include planning an imaging procedure and planning an irradiation procedure. An imaging procedure is planned in which an isocenter of the volume to be irradiated is located in the irradiation center of the imaging device. In that position (the irradiation position), the imaging is to be done for verifying the position of the patient in accordance with the irradiation planning. No beam is planned and applied in this irradiation position.

Planning an irradiation procedure may include defining an irradiation isocenter. One or more irradiation fields are planned. The planning of the irradiation procedure, for example, includes positioning the patient by the patient positioning device at the beginning of the irradiation procedure, in such way that the irradiation isocenter is located at an isocenter of the irradiation site. The irradiation isocenter is planned such that the patient is moved as close as possible to the beam exit without being endangered. The isocenter of the volume to be irradiated may be shifted from the imaging center to the irradiation isocenter. In the irradiation position, the actual radiation may take place.

Further imaging procedures and irradiation procedures may be planned, for example, including altered directions of incidence.

Figure 3:
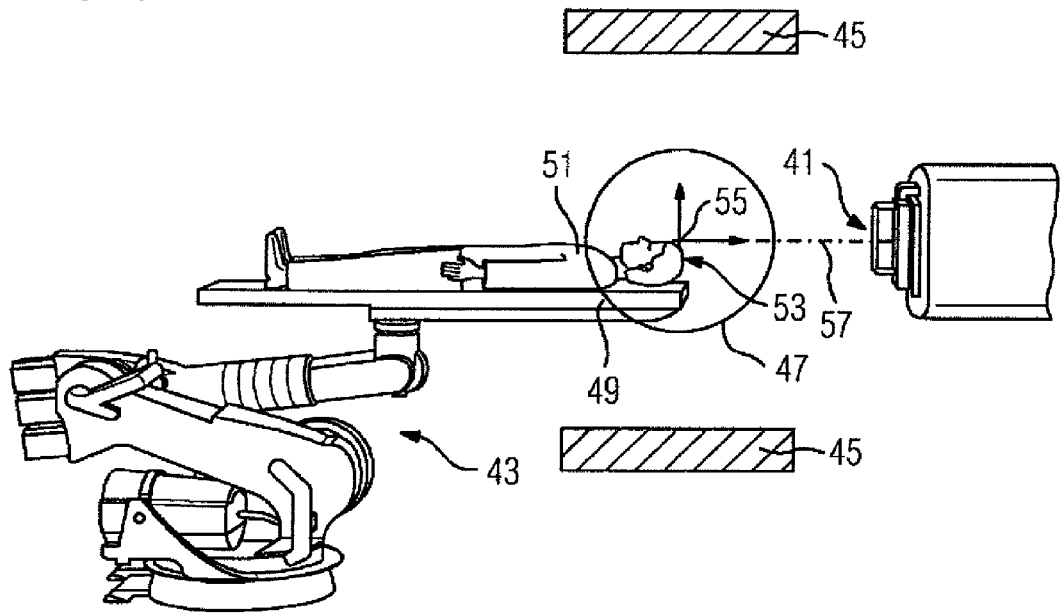
FIGS. 3 and 4 illustrate embodiments of an irradiation site, in which the patient is located in the imaging position and in the irradiation position, respectively.

FIG. 3 shows one example of a treatment chamber including a beam exit 41, a patient positioning device 43, and an imaging device 45 with an imaging volume 47. The patient positioning device 43 has a table 49, on which a patient 51 lies. The volume of the patient 51 that is to be irradiated is located, for example, inside a skull 53 of the patient 51. The imaging volume 47 has an imaging center 55. The imaging center 55 may be located on the center axis 57 of the particle beam, for example, at a distance of 100 cm from the beam exit 41. For position verification, an image of the volume to be irradiated, such as a 3D image, is now made with the imaging device 45. The selected spacing allows positioning the imaging device in all the positions required for the 39 imaging. The imaging device 45 may be rotated around the imaging center 55. The 3D image is calibrated with images used to plan the treatment planning. The patient 51 may be readjusted with the patient positioning device 43 into the position on which the treatment planning was based. The patient is then located in the imaging position defined in the therapy plan.

Figure 4:
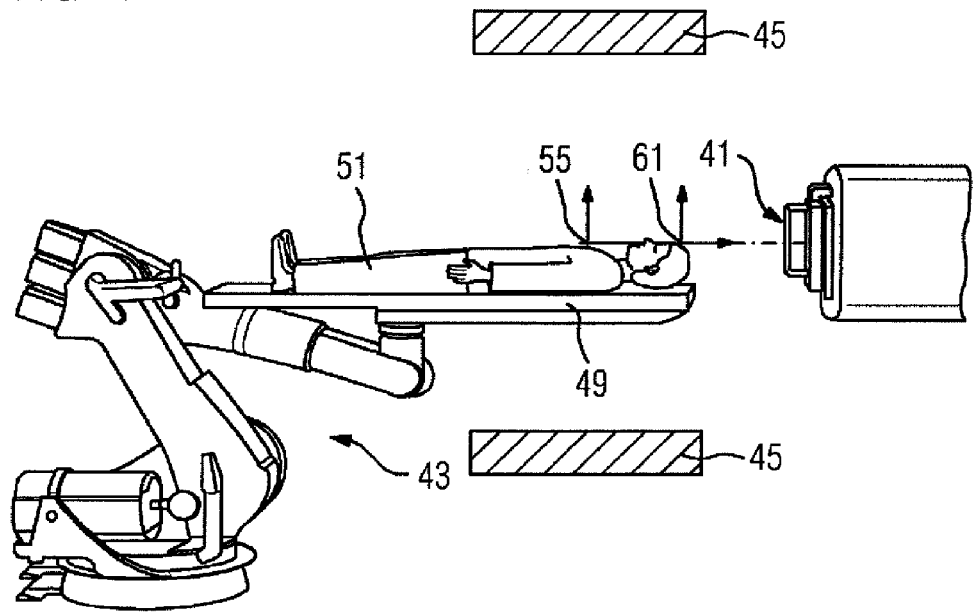

From the imaging position, the patient 51 is displaced into the irradiation position. The irradiation position is shown in FIG. 4. The volume to be irradiated, which was previously located around the imaging center 55, is now located around the irradiation isocenter 61 and can be irradiated voxel-specifically, for example, with a raster scanner.

The invention claimed is:

1. A particle therapy system for irradiating a volume to be irradiated with high-energy particles, the system comprising:
   a beam exit that delivers a particle beam from a radiation delivery and acceleration system, positioned in an irradiation position, the irradiation position being specified in a therapy plan relative to an irradiation isocenter of the particle therapy installation,
   an imaging device that verifies the location of the volume to be irradiated with respect to the particle beam,
   a patient positioning device that is operable to position the volume to be irradiated in the irradiation position, the imaging device being operable to verify the location of the volume to be irradiated in an imaging position that is spatially distant from the irradiation position, the patient positioning device being operable to automatically change position between the imaging position and the irradiation position,
   wherein the irradiation isocenter is adjustable in its distance from the beam exit.

2. The particle therapy installation as defined by claim 1, wherein the irradiation isocenter is adjustable as a function of the particle.

3. The particle therapy installation as defined by claim 2, wherein the particle may be a proton or carbon or oxygen ion.

4. The particle therapy installation as defined by claim 1, wherein the imaging position is located between the patient positioning device and the irradiation position.

5. The particle therapy installation as defined by claim 1, wherein the change of position from the imaging position to the irradiation position is based on a translational motion in the beam direction.

6. The particle therapy installation as defined by claim 5, wherein the imaging position includes an imaging center, which is located on a center axis of the particle beam.

7. The particle therapy installation as defined by claim 6, wherein the irradiation isocenter is located on a center axis of the particle beam.

8. The particle therapy installation as defined by claim 1, wherein the spacing between the irradiation position and the treatment position is less than 1 m.

9. The particle therapy installation as defined by claim 1, wherein the imaging device is operable to obtain a 3D data set.

10. The particle therapy installation as defined by claim 1, wherein the imaging device has dimensions which define a minimum spacing from the beam exit, and that the imaging device is located at least at this minimum spacing from the beam exit, and the minimum spacing is greater than the distance between the beam exit and the irradiation isocenter.

11. The particle therapy installation as defined by claim 1, wherein the imaging device is a C-arch X-ray machine or an imaging robot, and these are embodied rotatably about the imaging position, in particular about the imaging center, for 3D imaging; and that a minimum spacing from the beam exit is determined by the rotatability, and the imaging device is located at least at this minimum spacing from the beam exit.

12. The particle therapy installation as defined by claim 1, wherein the patient positioning device includes a robotically triggered treatment table, which is triggerable for displacing the patient from the imaging position to the irradiation position.

13. A therapy plan for irradiating a patient with particles of a particle therapy system, the therapy plan including:
   planning an imaging procedure in which an isocenter of a volume to be irradiated is located in an irradiation center of an imaging device;
   planning an irradiation procedure that includes defining an irradiation isocenter and positioning a patient using a patient positioning device in such way that the irradiation isocenter is located at an isocenter of the irradiation site; and
   positioning, with a positioning device, the patient between an imaging position for the imaging procedure and between an irradiation position for the irradiation procedure.

14. The therapy plan as defined by claim 13, comprising: a reference point for positioning the patient in the imaging position or irradiation position; and information about a relative position of the imaging position and irradiation position to one another.

15. The therapy plan as defined by claim 14, wherein the information about the relative position includes a displacement vector, which defines a displacement motion of a patient supporting device of the therapy installation, with which device the patient can be displaced from the imaging position into the irradiation position.

16. The therapy plan as defined by claim 15, wherein the displacement vector is parallel to a beam axis of a particle beam.

17. An irradiation method for irradiating a volume to be irradiated of a patient with high-energy particles from a therapy system, the method comprising:
   performing an imaging procedure for verification of the location of the volume to be irradiated, in the imaging procedure, imaging of the volume to be irradiated is performed using an imaging device, during which the patient is located in an imaging position;

performing an irradiation procedure, in which the patient, positioned in an irradiation position, is irradiated, and the irradiation position of the patient is specified by a therapy plan relative to an irradiation isocenter of the particle therapy installation and is located spatially distant from the imaging position;

changing a position of the patient is effected from the imaging position to the irradiation position or from the irradiation position to the imaging position using a patient positioning unit.

18. The irradiation method as defined by claim 17, wherein changing a position of the patient include displacing of the patient in or counter to the irradiation direction.

* * * * *